(12) United States Patent
Shen et al.

(10) Patent No.: US 7,351,854 B2
(45) Date of Patent: Apr. 1, 2008

(54) METHOD OF MANUFACTURING 1-CHLORO-2-METHYL-4-ACYLOXY-2-BUTENE DERIVATIVES

(75) Inventors: Runpu Shen, Xinchang (CN); Guoqi Yu, Xinchang (CN); Weidong Ye, Xinchang (CN); Kui Wang, Xinchang (CN); Xuejun Lao, Xinchang (CN)

(73) Assignees: Shaoxing University, Shaoxing (CN); Zhejiang Medicine Co., Ltd. Xinchang Pharmaceutical Factory, Xinchang (CN)

( * ) Notice: Subject to any disclaimer, the term of this patent is extended or adjusted under 35 U.S.C. 154(b) by 0 days.

(21) Appl. No.: 11/749,793

(22) Filed: May 17, 2007

(65) Prior Publication Data

US 2007/0270607 A1    Nov. 22, 2007

(30) Foreign Application Priority Data

May 17, 2006    (CN)    ................ 2006 1 0026619

(51) Int. Cl.
*C07C 67/02*    (2006.01)
(52) U.S. Cl. ..................................... 560/262
(58) Field of Classification Search ............... None
See application file for complete search history.

(56) References Cited

U.S. PATENT DOCUMENTS 4,745,229 A  *  5/1988  Otera et al. ............ 568/490

* cited by examiner

*Primary Examiner*—Paul A. Zucker
(74) *Attorney, Agent, or Firm*—Matthias Scholl P.C.; Matthias Scholl

(57) ABSTRACT

1-Chloro-2-methyl-4-acyloxy-2-butene derivatives can be synthesized in good yields and high purity starting from isoprene and employing a chlorohydrin formation reaction in a system made of N-chloroisocyanuric acid derivatives and water, followed by esterification and rearrangement of the crude product mixture.

14 Claims, No Drawings

METHOD OF MANUFACTURING 1-CHLORO-2-METHYL-4-ACYLOXY-2-BUTENE DERIVATIVES

CROSS-REFERENCE TO RELATED APPLICATIONS

This application claims priority to Chinese Patent Application No. 200610026619.5 filed on May 17, 2006, the contents of which are incorporated herein by reference.

BACKGROUND OF THE INVENTION

1. Field of the Invention

The invention relates to a method of manufacturing 1-chloro-2-methyl-4-acyloxy-2-butene derivatives, which are important precursors of Vitamin A acetate.

2. Description of the Related Art

Vitamin A and its derivatives are used in great quantities as medicines, food additives and feed additives. One of the most important Vitamin A derivatives is Vitamin A acetate. The key intermediate in the C15+C5 Wittig-based synthesis of Vitamin A acetate is 4-acetyloxy-2-methyl-2-butene-1-aldehyde (a C5 aldehyde of MW 142) (Tanaka, U.S. Pat. No. 5,424,478, Process for producing Vitamin A Derivatives, [P] 1995; Tanaka, et al., JP Pat. No. 06,329,623, Preparation of Vitamin A Derivatives, [P] 1994; Zutter, Ulrich, EP 648,735, Preparation of an intermediate for Vitamin A acetate, [P] 1995).

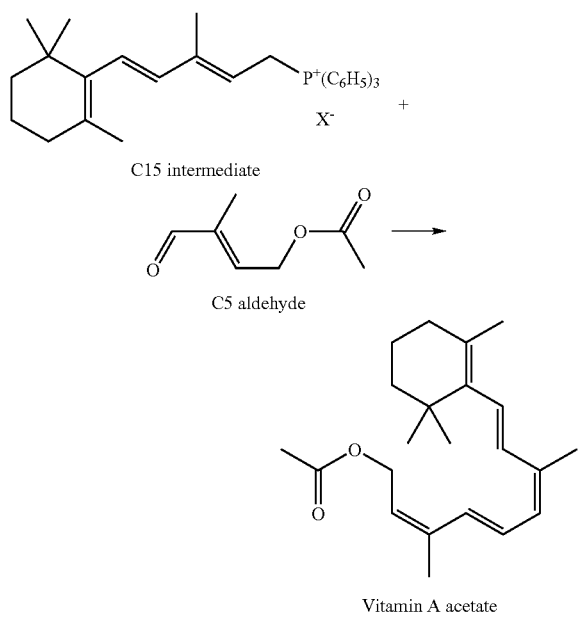

Since H. Pommer at BASF reported an industrial scale synthesis of the C5 aldehyde (H. Pommer, A. Nurrenbach, Pure. Appl. Chem., Industrial synthesis of Terpene compounds, [J] 1975, 43, 527), there has been no shortage of improvements. Among them, use 1-chloro-2-methyl-4-acetyloxy-2-butene to prepare the C5 aldehyde is well documented (Tanaka, et al., JP Pat. 06,329,623, Preparation of Vitamin A Derivatives, [P] 1994; Ven Kataratnam, Revannuru V., et al., IN Pat. IN 168,539, An improved process for the preparation of 4-acetoxy-2-methyl-2-butenal, [P] 1988; Kaneko, Tatsuhiko, et al., JP 07,61,948, Preparation of α,β-unsaturated aldehydes, [P] 1995; Babler, James. H., PCT. Int. Appl. 7900,485, E-4-Acetoxy-2-methyl-2-butenal, [P] 1979; Babler, James H., U.S. Pat. No. 4,175,204, E-4-Acetoxy-2-methyl-2-butenal, [P] 1979; Babler, James H., J. Org. Chem., Facile synthesis of 4-acetoxy-2-methyl-2-butenal, a Vitamin A precursor [J] 1979, 44(10), 1716-17). This it is safe to say that 1-chloro-2-methyl-4-acetyloxy-2-butene is an important intermediate in the synthesis of Vitamin A acetate.

When methyl is replaced by a different alkyl in the first equation below, it yields important intermediates for the synthesis of various other Vitamin A derivatives.

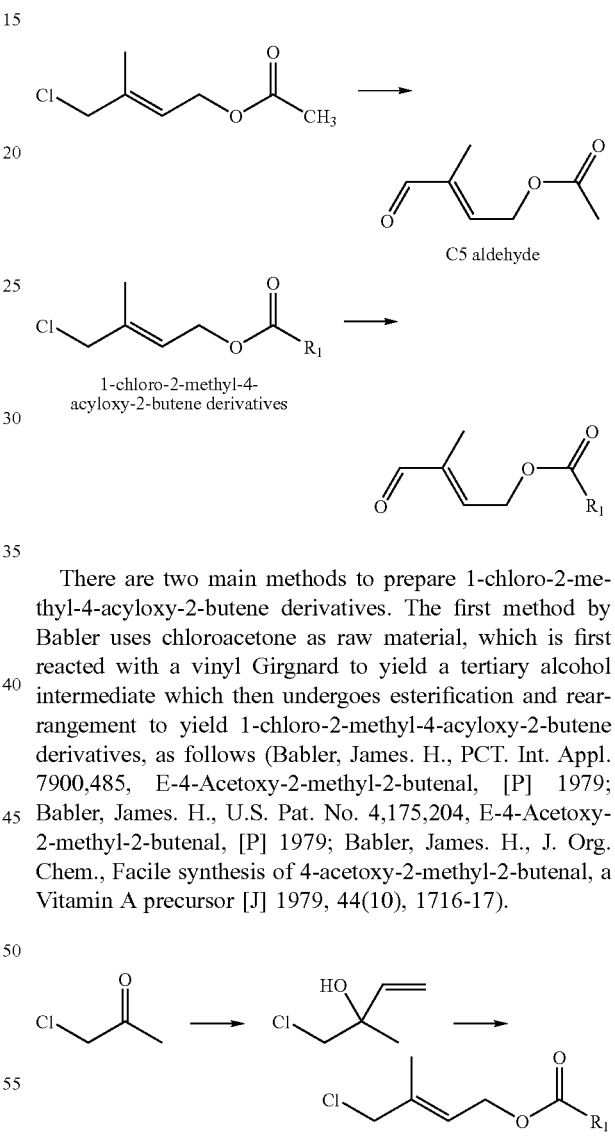

There are two main methods to prepare 1-chloro-2-methyl-4-acyloxy-2-butene derivatives. The first method by Babler uses chloroacetone as raw material, which is first reacted with a vinyl Girgnard to yield a tertiary alcohol intermediate which then undergoes esterification and rearrangement to yield 1-chloro-2-methyl-4-acyloxy-2-butene derivatives, as follows (Babler, James. H., PCT. Int. Appl. 7900,485, E-4-Acetoxy-2-methyl-2-butenal, [P] 1979; Babler, James. H., U.S. Pat. No. 4,175,204, E-4-Acetoxy-2-methyl-2-butenal, [P] 1979; Babler, James. H., J. Org. Chem., Facile synthesis of 4-acetoxy-2-methyl-2-butenal, a Vitamin A precursor [J] 1979, 44(10), 1716-17).

The second method uses isoprene as raw material, which reacts with sodium hypochlorite in a chlorohydrins formation reaction to yield a mixture of 1,2 and 1,4 addition products. The mixture then undergoes esterification and rearrangement to yield 1-chloro-2-methyl-4-acyloxy-2-butene (Tanaka, et al., JP 06,329,623, Preparation of Vitamin A Derivatives, [P] 1994; Kuroda, Noritaka, et al., JP. 06,345, 689, Preparation of butenal derivatives, [P] 1994).

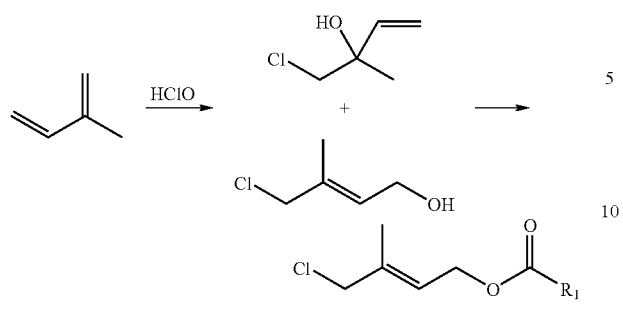

The second method is potentially more valuable industrially because of its low cost and facile process conditions. For example, to maintain the pH during the chlorohydrin reaction, $CO_2$, $H_2SO_4$, HCl or $CH_3COOH$ can be added. However, we have found through experiments that the content of the product in this process is low and the yield is low as well.

Ordinarily, olefin chlorohydrin formation reaction can be realized by adding chlorine to an aqueous suspension of calcium hydroxide, making use of the active hypochlorous acid formed. However, we have found through experiments that the content of products obtained in this process is low, perhaps owing to the fact that the existence of free chlorine and other heteroions provokes a side reaction of the olefin's double bond, such as a dichloroaddition, etc. This increases impurities.

Therefore, it is presumed that the chlorohydrin reaction can be modified by proceeding in a more mild system, which contains fewer heteroions. N-chloroisocyanuric acid series compounds (comprising trichloroisocyanuric acid A, dichloroisocyanuric acid B, a sodium salt of dichloroisocyanuric acid C, and a potassium salt of dichloroisocyanuric acid D, or other metal-salts thereof, dichloroisocyanuric acid sodium salt contained crystal water, monochloroisocyanuric acid and its metal-salt etc.; or complexes made up of two or more compounds mentioned above) widely serve as detergents, cleaning agents, bactericidal and sanitizing compounds of public use and domestics. At present, this series compound begins to find use in organic chemistry.

Structural formula of several main kinds of N-chloroisocyanuric acid series compounds are illustrated below:

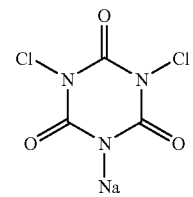

A

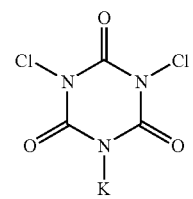

B

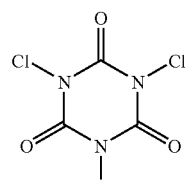

C

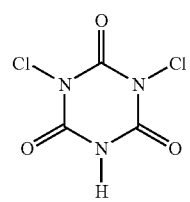

D

Among these are, trichloroisocyanuric acid (A) (trichlorotriazinetriketone, molecular formula: $Cl_3(CNO)_3$, the content of available chlorine about 90%) which has the highest content of available chlorine in all solid matter, organic and inorganic alike; sodium salt of dichloroisocyanuric acid (C) (molecular formula: $NaCl_2(CNO)_3$, the content of available chlorine about 62.5%); and its crystal water form (molecular formula: $NaCl_2(CNO)_3.2H_2O$, the content of available chlorine about 55.5%), all commonly and widely used.

The N-chloroisocyanuric acid derivatives can react with water and generate hypochloric acid and corresponding derivatives of cyanuric acid. For example of trichloroisocyanuric acid reacts with water as follows:

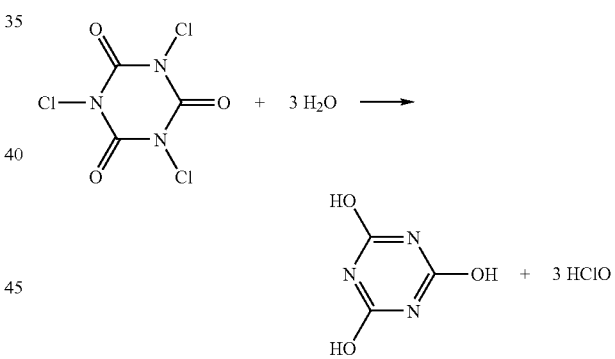

This reaction is rapid and thorough, and all the available chlorine can be made full use of.

Accordingly, we have tried our best to make use of the N-chloroisocyanuric acid series of compounds in place of sodium hypochlorite and calcium hypochlorite which have been mentioned above in the chlorohydrin formation reaction. We have discovered during these endeavors that content of the desired product in the reaction mixture and the yield improved greatly and the amount of waste reduced enormously, both of which demonstrate a great industrial value to these reagents.

BRIEF SUMMARY OF THE INVENTION

In one aspect of the invention, provided is an improved method for the synthesis of 1-chloro-2-methyl-4-acyloxy-2-butene derivatives. In certain embodiments, isoprene is used as starting material, and undergoes chlorohydrin reaction in the system made up of N-chloroisocyanuric acid series of compounds and water. Then the crude product mixture reacts with an acetic anhydride or an acyl halide to undergo esterification and rearrangement to yield a 1-chloro-2-methyl-4-acyloxy-2-butene derivative in good yields and high purity.

The structure of the 1-chloro-2-methyl-4-acyloxy-2-butene derivative is as follows:

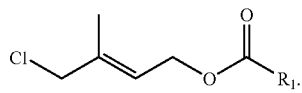

In certain embodiments of the above formula, $R_1$ represents alkyl, e.g., saturated on unsaturated $C_1$-$C_{20}$ alkyl; preferably, alkyl, cycloalkyl, alkene, cycloalkene, alkyne, etc.; more preferably, $C_1$-$C_{20}$ alkyl, such as, methyl, ethyl, propyl, butyl, pentyl, hexyl, heptyl, octyl, nonyl, decyl, and undecyl to eicoxyl, etc.; and most preferably methyl and pentadecyl. When $R_1$ is methyl, the vitamin A acetate is obtained, and when $R_1$ is pentadecyl, vitamin A palmitate is obtained.

The anhydrides used in embodiments of this invention are acetic anhydride and propionic anhydride. The acyl halide compound used in embodiments of this invention is palmityl chloride.

According to the process of this invention, a mild reaction system with a high content of available chlorine and fewer heteroions is provided. The reaction system is improved which leads to good yields and high purity of desired products.

Ordinarily, the content of available chlorine in an aqueous solution of sodium hypochlorite is about 10%, and not higher than 15%; in calcium hypochlorite solid (bleaching powder) about 30%; in dichloroisocyanuric acid about 55-60%; and trichloroisocyanuric acid about 90%.

N-chloroisocyanuric acid derivatives sold commercially, which are applicable for use in the methods of this invention include without limitation trichloroisocyanuric acid; dichloroisocyanuric acid; sodium salt of dichloroisocyanuric acid; hydrate of the sodium salt of dichloroisocyanuric acid; potassium salt of dichloroisocyanuric acid; hydrate of the potassium salt of dichloroisocyanuric acid; calcium salt of dichloroisocyanuric acid; hydrate of the calcium salt of dichloroisocyanuric acid; magnesium salt of dichloroisocyanuric acid; hydrate of the magnesium salt of dichloroisocyanuric acid; and monochloroisocyanuric acid.

In certain embodiments of the invention, two or more of the N-chloroisocyanuric acid derivatives sold commercially can mix at a free ratio. In certain embodiments of the invention, the mixtures will have a better stability and feature a slow-release of chlorine. Moreover, the mixture of N-chloroisocyanuric acid compounds and other components also have a similar effect, and are included in the bounds of the invention. Generally, the higher the content of the available chlorine and the fewer heteroions, the better the result.

In order to make the reaction of the N-chloroisocyanuric acid derivatives with water to proceed to completion and to make full use of the available chlorine, the molar ratio of water to N-chloroisocyanuric acid compounds is about 1-50:1. For example, more than 3 moles of water should be used when 1 mole of trichloroisocyanuric acid is used; and more than 2 moles of water are needed when using 1 mole of dichloroisocyanuric acid.

As reagent, water is added all at one time, or it is added gradually, or a part is added at first and the rest gradually. N-chloroisocyanuric derivatives are added all at one time, or are added gradually, or part is added at first and the rest gradually. It is preferred to add N-chloroisocyanuric derivatives gradually to control the reaction. Isoprene is added all at one time or it is added gradually.

This reaction is carried out at a temperature of from −50° C. to 50° C. A preferred temperature is from −5° C. to 10° C. Byproducts will increase largely at higher temperature, but too low of a temperature is difficult to attain on industrial scale. The reaction is carried out in an organic or inorganic solvent, for example an alcohol, including but not limited to methanol, ethanol and propanol; an ester such as methyl acetate, ethyl acetate or other kinds of acid esters; a ketone such as propanone, butanone or pentanone; an alkyl halide such as dichloromethane, chloroform or tetrachloromethane; an alkyl such as cyclohexane, n-hexane; an aromatic solvent such as benzene or toluene; an ether such as diethyl ether or tetrahydrofuran; an organic acid such as acetic acid or formic acid, or an aprotic solvent such as DMF, DMSO etc.

After the chlorocyanuric acid (or its derivates such as sodium salt) has undergone reaction, it can be recovered and reused, as follows:

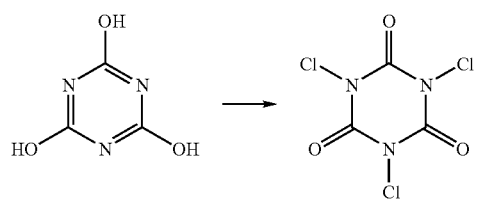

Therefore, not only the cost reduced, but also waste is decreased or even no waste discharged, which is quite appropriate for an industrial process. In comparison, when sodium hypochlorite used as raw material, much waste water containing sodium chloride is produced, and when calcium hypochlorite used, waste calcium chloride is created.

DETAILED DESCRIPTIONS OF THE INVENTION

Analytical apparatus: Combination of gas chromatography and mass spectrometry, MS5973N-GC6890N (Agilent Co. America); Nuclear magnetic resonance apparatus, AVANCE DMX 500 (TMS interior label); Infrared spectrometry apparatus, NICOLET 360FT-IR.

EXAMPLES

Example 1

Preparation of a mixture of 1-chloro-2-hydroxy-2-methyl-3-butylene and 1-chloro-2-methyl-4-hydroxy-2-butylene A 500 mL three neck flask equipped with a thermometer and a solid feed inlet was charged with 68 g (1 mole) of isoprene, 100 mL $H_2O$, 0.5 g hydroquinone (polymerization inhibitor), then put it into a cooling bath. The temperature was kept at 0-5° C. 58 g (0.25 moles) trichlorominocyanuric acid (90% available chlorine) were added with stirring within about 1 hour, and stirring continued for another 1 h at the same temperature. Then the reaction mixture was filtered, and the filter cake washed with 15 mL $H_2O$ and dried. The weight of the obtained white solid was 31 g (0.24 moles). The filtrates were combined. The organic layer was separated and the unreacted isoprene recovered under reduced pressure below 41° C. to yield 90 g of the crude title products. GC analysis indicated the total content of crude product was 92.5%, and the yield was 92.1%. The recovered unreacted isoprene could be reused in the next reaction directly. The aqueous layer was 99.5 g. The aqueous also could be reused in the next reaction directly. The crude products were separated by rectification and the two pure product analyzed separately:

1-chloro-2-hydroxy-2-methyl-3-butylene: IR(v/cm$^{-1}$): 3430(—$CH_2OH$), 1640 (—CH=$CH_2$); NMR δ (ppm): 1.38 (s, 3H, $CH_3$), 1.93(1H, —OH), 3.55(2H, Cl—$CH_2$—), 5,29 (dd, 2H, =$CH_2$), 5.91(1H, —CH=); DEPT: δ (ppm): 138.142 (2H, =$CH_2$), 116.051(1H, —CH=), 49.887(3H, —$CH_3$), 21.611(2H, —$CH_2$—Cl);

1-chloro-2-methyl-4-hydroxy-2-butylene: IR(v/cm$^{-1}$): 3430 (—$CH_2OH$), 1640 (—C=CH—); NMR δ(ppm): 1.38 (s, 3H, $CH_3$), 2.15 (1H, —OH), 3.55 (2H, Cl—$CH_2$—), 5.29 (dd, 2H, =$CH_2$), 5.91(1H, —CH=); DEPT: δ(ppm): 141.469(1H, =CH—), 114.051(2H, —$CH_2$—OH), 54.135 (2H, —$CH_2$—Cl), 25.488(3H, —$CH_3$).

Example 2

Preparation of
1-chloro-2-methyl-4-acetyloxy-2-butene by
esterification and rearrangement A 250 three neck flask was charged with 80 g acetic anhydride (0.78 moles) and 63 g crude product (content 92.5%, 0.48 moles) obtained in upper step; 1 g para-toluenesulfonate added under stir, then heated to 60° C. and stir for 5 h. Cooled to room temperature, 100 mL $H_2O$ added and stir 10 min, stratified, waste water was removed. Organic layer washed with 100 mL $H_2O$, stratified, 63 g crude product was obtained (content 90% by G.C.), after rectification a colorless transparency liquid 55 g (content 93.5% by G.C.) obtained, yield 66%.

GC-MS(m/e): 127, 102, 84, 67, 43(100%), 29; IR(v/cm$^{-1}$): 1735 (—OCO—), 1230 (C—O—CO—, $v^{as}$), 1035(—C—O—CO—, $v^s$); $^1$HNMR(500 MHz, CDCl$_3$) δ(ppm): 1.83(s, 3H, —$CH_3$), 2.06(s, 3H, —COCH$_3$); 4.01(2H, Cl—$CH_2$—); 4.62(2H, =$CH_2$); 5.69(1H, =CH—); DEPT: δ(ppm): 124.019(1H, =CH—); 62.535(2H, —OCH$_2$—); 50.135(2H, —$CH_2$—Cl); 21.106(3H, —$CH_3$); 14.807(3H, —$CH_3$).

Example 3

Materials molar ratio, reaction temperature and post treatment were the same as in Example 1, the difference was that the water used came from the waste water of example 1. Obtained crude product 93 g, the total content of product was 89.5% by GC analysis, the yield was 92.1%. The white filter cake after dried was 30.5 g white powder (0.236 moles), waste water 98 g.

Example 4

Materials molar ratio, reaction temperature and post treatment were the same as in Example 1, the difference was that the water used came from the waste water of example 3. Obtained crude product 94.5 g, the total content of product was 90.5% by GC analysis, yield 94.6%.

Example 5

A 500 mL three-neck flask with a thermometer and a solid feed inlet was charged with 68 g (1 mole) isoprene, 20 mL $H_2O$, 100 mL methanol, and 0.2 g hydroquinone (polymerization inhibitor), then put into a cooling bath. The temperature was kept at 0-5° C. 58 g (0.25 moles) trichlorominocyanuric acid (90% available chlorine) was added with stirring over about 0.5 h, then the reaction mixture was stirred at the same temperature for 1 hour. The reaction mixture was filtered, the filter cake washed with 15 mL methanol and dried. The weight of the obtained white solid was 29 g (0.225 mole). The filter liquors were combined. The organic layer was separated and the unreact isoprene recovered under reduced pressure below 40° C. 85 g of crude product was obtained. GC analysis indicated that the total content of crude product was 93.5%, the yield was 87.9%. The crude product could be used in the next reaction directly.

Example 6

A 1000 mL three neck flask with a thermometer and a solid feed inlet was charged with 68 g (1 mole) of isoprene, 20 mL $H_2O$, and 0.2 g hydroquinone (polymerization inhibitor). The flask was placed into a cooling bath. The temperature was kept at 0-5° C. 88 g (0.4 mole) of sodium dichlorocyanurate (62% available chlorine) dissolved in 400 mL $H_2O$ was added dropwise to the flask over about 1 hour. The reaction mixture was then stirred for 1 h at the same temperature. A white suspension was obtained. After stratification, the organic layer was separated and the unreacted isoprene recovered under reduced pressure below 40° C. 75 g of a crude product was obtained. G.C. analysis indicated that the total content of product was 90.5%, and yield was 75.1%.

Example 7

Materials molar ratio, reaction temperature, and post treatment were the same as in Example 6, the difference was that the water was the waste water of example 6. Obtained 89 g of crude product. GC analysis indicated that the total content of product was 89.5%, yield was 87.1%.

Example 8

Preparation of
1-chloro-2-methyl-4-propionyloxy-2-butene by
esterification and rearrangement A 250 mL three-neck flask was charged with 80 g propionic anhydride (0.62 mole) and 60.5 g crude product (content 89.5%, 0.45 mole) obtained in the last step. 1 g of para-toluenesulfonate was added under stirring. The reaction mixture was then heated to 55° C. and stir for additional 5 h. The reaction mixture was cooled to room temperature. 100 mL $H_2O$ was added and stirred for 10 min, stratified, waste water was removed. Organic layer was washed with 100 mL $H_2O$, stratified, 63 g crude product was obtained (content 81% by G.C.). After rectification a colorless transparent liquid 45 g (content 91.5% by G.C.) was obtained, yield 52%.

$^1$HNMR(500 MHz, CDCl$_3$) δ (ppm): 1.13(tri, 3H, —$CH_3$), 2.06(s, 3H, —COCH$_3$) ; 2.35(tetra, 2H, —COCH$_2$—); 4.01(2H, Cl—$CH_2$—); 4.62(2H, =$CH_2$); 5.59(1H, —CH=).

Example 9

Preparation of 1-chloro-2-methyl-4-palmityloxy-2-butene by esterification and rearrangement A 250 mL three neck flask was charged with 100 g palmityl chloride (0.36 mole) and 60 g crude product (content 90.5%, 0.45 mole) obtained in Example 6. 1 g para-toluenesulfonate was added under stirring, then heated to 55° C. and stirred for 5 h. Cooled to room temperature. 100 mL of $H_2O$ were added and stirred for 10 min. Stratified. Waste water was removed. Organic layer was washed with 100 mL $H_2O$ Stratified. 83 g of crude title product was obtained, after separation by silica gel column chromatography (ethyl acetate: n-hexane=1:99) a colorless transparent liquid 54 g (0.15 mole) was obtained, yield 42%.

Example 10

A 1000 mL three neck flask equipped with a thermometer and a solid feed inlet was charged with 68 g (1 mole) of isoprene, 20 ml $H_2O$, 100 mL ethyl acetate, and 0.2 g hydroquinone (polymerization inhibitor). The flask was put into a cooling bath. The temperature was kept at 0-5° C. A solution of 88 g (0.4 mole) sodium dichlorocyanurate (62% available chlorine) dissolved in 400 mL $H_2O$ was added dropwise over about 1 hour. It was then stirred for 1 h additionally at the same temperature upon which a white suspension was obtained. After stratification the organic layer was separated and the unreacted isoprene recovered under reduced pressure below 40° C. 78 g of crude product was obtained. G.C. analysis indicated that the total content of product was 91.5%, yield 79%.

Example 11

A 1000 mL three neck flask equipped with a thermometer and a solid feed inlet was charged with 68 g (1 mole) of isoprene, 20 mL $H_2O$, 100 mL acetone and 0.2 g of hydroquinone (polymerization inhibitor). The flask was then placed into a cooling bath. The temperature was kept at 0-5° C. A mixture made up of 29 g (0.125 moles) of trichlorominocyanuric acid (90% available chlorine) and 44 g (0.2 mole) sodium dichlorocyanurate (62% available chlorine) was added over a period of about 1 hour. It was then stirred for 1 h at the same temperature and a white suspension was obtained. The reaction mixture was filtered, the cake was washed with 15 mL acetone. The filtrate was distilled under reduced pressure below 40° C. to recovery the unreacted isoprene and to obtain 85 g of the crude product. G.C. analysis indicated that the total content of product was 93.5%, yield 87.9%. The product was used in the next reaction directly.

Example 12

Materials molar ratio, reaction temperature and post treatment were the same as in Example 11, the difference was that the solvent used was a mixture of 60 mL THF and 60 ml cyclohexane. Obtained 83 g of crude product. The total purity was 92.5% by GC analysis, the yield was 84.9%.

Example 13

Materials molar ratio, reaction temperature and post treatment were the same as in Example 11, the difference was that the solvent used was a mixture of 60 mL DMF and 60 mL acetic acid. The reaction mixture was filtered, the filtrate added to 200 mL water and 200 mL methylene dichloride was subsequently added. After stratifying, waste water was removed, the organic layer was separated and it was distilled under reduced pressure below 40° C. to recover the unreacted isoprene. 65 g of te crude product was obtained; the total content of product (purity) was 93.5% by GC analysis, the yield was 67.2%.

Comparison Example 1

Chlorohydrin Reaction of Isoprene in a Sodium Hypochlorite and Acetic Acid System A 1000 mL four neck flask equipped with a thermometry and two dropping funnels was charged with 68 g (1 mole) isoprene, 100 mL $H_2O$, 0.2 g hydroquinone (polymerization inhibitor). The flask was then placed into a cooling bath. 150 g of 50% acetic acid and 500 g of 10% sodium hypochlorite were added into the two dropping funnels, respectively. It was stirred at the temperature from 0° C. to 5° C. The two liquids in dropping funnels were added dropwise each, measuring the pH continuously to maintain the pH value at between 7.5 and 8.5 (use pH indicator paper or pH meter). The two liquids were fully added over a period of about 3 hours. Then, the same temperature was kept and it was stirred for 1 h. Stratified. Obtained 88 g of crude products. GC analysis indicated that the total content of crude product (purity) was 65%. The unreacted olefin content was 20%. The unreacted isoprene was recovered under reduced pressure below 40° C. 76 g of crude product was obtained. G.C. analysis indicated that the total content of product was 83%, and the yield was 52%.

Comparison Example 2

Chlorohydrin Reaction of Isoprene in a Sodium Hypochlorite and Sulfuric Acid System Materials molar ratio, reaction temperature and post treatment were the same as in Comparison Example 1. The difference was that 50% acetic acid aqueous solution was substituted by 75 g of 50% sulfuric acid aqueous solution. The measured pH value changed constantly. It was difficult to maintain the pH value constant at first, and the pH value was controlled to the best of our abilities at between 6 and 8.5. After post treatment, obtained 63 g of crude product. G.C. analysis indicated that the total content of product (purity) was 76.1%, and the yield was 28.6%.

What is claimed is:

1. A method of manufacturing a 1-chloro-2-methyl-4-acyloxy-2-butene derivative having the following structure:

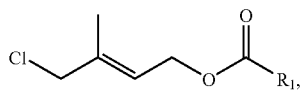

wherein $R_1$ is an alkyl,
comprising
(1) reacting isoprene with at least one N-chloroisocyanuric acid derivative and water to obtain a mixture of 1-chloro-2-hydroxy-2-methyl-3-butylene and 1-chloro-4-hydroxy-2-methyl-2-butylene;

(2) reacting the mixture obtained in step (1) under acidic conditions with an acid anhydride or an acyl halide to undergo esterification and rearrangement to yield the 1-chloro-2-methyl-4-acyloxy-2-butene derivative having the following structure:

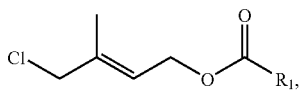

wherein R₁ is an alkyl.

2. The method of claim 1, wherein N-chloroisocyanuric acid derivative is selected from the group of trichloroisocyanuric acid; dichloroisocyanuric acid, sodium salt of dichloroisocyanuric acid; hydrate of the sodium salt of dichloroisocyanuric acid; potassium salt of dichloroisocyanuric acid; hydrate of the potassium salt of dichloroisocyanuric acid; calcium salt of dichloroisocyanuric acid; hydrate of the calcium salt of dichloroisocyanuric acid; magnesium salt of dichloroisocyanuric acid; hydrate of the magnesium salt of dichloroisocyanuric acid; N-monochloroisocyanuric acid, sodium salt of N-monochloroisocyanuric acid; hydrate of the sodium salt of N-monochloroisocyanuric acid; potassium salt of monochloroisocyanuric acid; hydrate of the potassium salt of monochloroisocyanuric acid; and mixtures thereof.

3. The method of claim 1, wherein said acid anhydride in step (2) is acetic anhydride or propionic anhydride; and said acyl halide in step (2) is palmityl chloride.

4. The method of claim 1, wherein water is provided at a molar ratio with respect to said N-chloroisocyanuric acid derivative of from 50:1 to 1:1.

5. The method of claim 1, wherein water is provided at a molar ratio with respect to said N-chloroisocyanuric acid derivative of greater than 1:1.

6. The method of claim 5, wherein
when said N-chloroisocyanuric acid derivative is N-trichloroisocyanuric acid, water is provided at a molar ratio with respect to said N-trichloroisocyanuric acid of greater than 3:1; and
when said N-chloroisocyanuric acid derivative is N-dichloroisocyanuric acid, water is provided at a molar ratio with respect to said N-dichloroisocyanuric acid of greater than 2:1.

7. The method of claim 1, wherein water in added in step (1) all at one time; gradually; or a portion at first and the rest gradually.

8. The method of claim 1, wherein step (1) and/or step (2) is carried out at a temperature of from −50° C. to 50° C.

9. The method of claim 1, wherein reactions in step (1) and/or step (2) are carried out at a temperature of from −5° C. to 10° C.

10. The method of claim 1, wherein reactions in step (1) and/or step (2) are carried out in an organic or an inorganic solvent.

11. The method of claim 1, wherein R₁ is methyl or pentadecyl.

12. The method of claim 1, wherein reactions in step (1) and/or step (2) are carried out in a solvent.

13. The method of claim 12, wherein said solvent is selected from an alcohol, an ester, a ketone, an alkyl halide, an alkyl, an aromatic solvent, an ether, an organic acid, an inorganic acid, or an aprotic solvent, or mixtures thereof.

14. The method of claim 13, wherein said solvent is selected from methanol, ethanol, propanol, methyl acetate, ethyl acetate, propanone, butanone, pentanone, cyclohexane, n-hexane, benzene, methylbenzene, diethyl ether, tetrahydrofuran, DMF, DMSO, dichloromethane, chloroform, tetrachloromethane, acidic acid or formic acid, or mixtures thereof.

* * * * *